(12) United States Patent
Melki

(10) Patent No.: US 8,088,134 B2
(45) Date of Patent: Jan. 3, 2012

(54) OPHTHALMIC MARKER FOR SURGICAL RETINAL VITREOUS PROCEDURES

(76) Inventor: Toufic S Melki, Rockville, MD (US)

(*) Notice: Subject to any disclaimer, the term of this patent is extended or adjusted under 35 U.S.C. 154(b) by 590 days.

(21) Appl. No.: 12/232,118

(22) Filed: Sep. 11, 2008

(65) Prior Publication Data

US 2009/0043322 A1 Feb. 12, 2009

Related U.S. Application Data

(63) Continuation-in-part of application No. 11/397,368, filed on Apr. 5, 2006, now abandoned.

(51) Int. Cl.
*A61F 9/00* (2006.01)

(52) U.S. Cl. ........................................ 606/166

(58) Field of Classification Search ............... 606/166, 606/67, 107, 167, 185, 186, 210; 33/23.11, 33/27.031, 27.032, 41.4, 41.6, 44, 501.17, 33/501.18, 501.45; 30/279.2, 280, 284, 285, 30/287, 294, 299, 314, 322, 323
See application file for complete search history.

(56) References Cited

U.S. PATENT DOCUMENTS

| | | | | |
|---|---|---|---|---|
| 5,484,447 A * | 1/1996 | Waldock et al. | ............... | 606/107 |
| 5,547,468 A * | 8/1996 | Simon et al. | ................... | 604/21 |
| 6,142,994 A * | 11/2000 | Swanson et al. | ................ | 606/41 |
| 6,514,238 B1 * | 2/2003 | Hughes | ............................. | 606/1 |
| 2007/0038234 A1 * | 2/2007 | Yaldo | ............................ | 606/166 |
| 2007/0083221 A1 * | 4/2007 | Carda | ............................ | 606/166 |

* cited by examiner

*Primary Examiner* — Gary Jackson
*Assistant Examiner* — Lindsey Bachman
(74) *Attorney, Agent, or Firm* — John Richardson

(57) ABSTRACT

The invention relates to ophthalmology surgical procedures, and specifically to vitreous retinal surgical procedures for marking positions for incision/injection sites on the scleral surface of the eye. The types of ophthalmic vitreous surgical procedures for which are applicable include but not limited to, vitrectomies performed in hospital operating rooms and vitreous injections are routinely performed in doctor's offices for a variety of procedures to treat abnormal eye conditions. The invention discloses a range of scleral limbal marker for adult human patients, pediatric patients, and domestic and other animals. The invention discloses markers in materials capable of sterilization and for markers in materials suitable for disposal and packaged in vacuum sealed packages.

20 Claims, 9 Drawing Sheets

Figure 4:
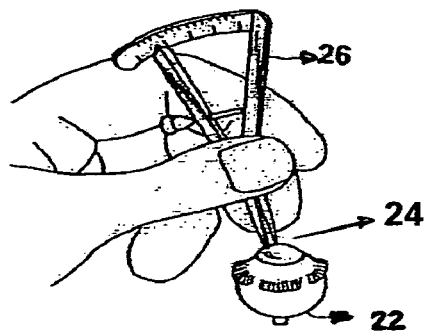

FIGURE 4 Example of prior art sclera marking tool

X = DISTANCE BETWEEN POINTER 18 & 20

OPHTHALMIC MARKER FOR SURGICAL RETINAL VITREOUS PROCEDURES

The invention disclosed herein is a Continuation-in-Part of application Ser. No. 11/397,368, filed Apr. 5, 2006 now abandoned.

BACKGROUND OF THE INVENTION

The invention herein disclosed describes an ophthalmic marker identified as the 'Melki Marker', and relates to ophthalmology, and specifically to retinal surgical vitreous procedures for marking positions for incision/injection sites on the scleral tissue. The types of ophthalmic vitreous surgical procedures for which the 'Melki Marker' are applicable include but not limited to, vitrectomies performed in hospital operating rooms and in doctor's offices where vitreous injections are routinely performed for a variety of procedures to treat abnormal eye conditions.

In executing surgical complicated procedures on tissue within the human eye, and for other animals such as horses, domestic cats and dogs, it is necessary to accurately locate the position of incision locations on the scleral surface of the eye.

In order to prevent having surgical intervention taking place too far from the location to be operated on, or at a wrong angle or in an improper plane or inclination, it is necessary to mark the location as accurately and precisely as practical.

BRIEF SUMMARY OF THE INVENTION

The specific procedure is an ophthalmic procedure wherein it is essential to locate the point of incision on the sclera limbal tissue surface to ensure that the location is safe to enter the Pars Plana region. In the event that the location is outside the Pars Plana region serious medical complications could result, such as lens damage, and thus creating a cataract. Another complication can be a retina tear or detachment. For the adult human eye the safe Pars Plana region is at a fixed dimension of 3.5 mm from the outer edge of the iris, also known as limbus.

The procedure using existing caliper markers consists of defining an incision site on the surface of the eyeball by initially drying the surface of the eye with sterilized disposable "Q" tip cotton swabs and marking the incision point with caliper pointers set by thumbscrew setting caliper scale at the required position to suit the patient. The set pointers are applied with ink by a nurse using sterilized blue pen from an epidermic labeler, such as #150 available from Devon Inc., or equivalent non-toxic, waterproof, absorbable ink or stain. In this manner the ink soaked pointers can be placed on the eye ball to mark the incision site.

It will be evident that in such a procedure, it is essential that the caliper pointers are correctly set by a nurse in attendance, further checked by the surgeon before carefully aligning caliper mechanism on the scleral in each instance and that the whole procedure is time consuming.

The marker types that have been used in these ophthalmic procedures are disclosed for example, by Simon in U.S. Pat. No. 5,090,955, and by manufacturer Storz Gmbh in Germany in the Model # E2404—Castroviejo Caliper. These markers are based on a caliper adjustment range of between 0 mm to 20 mm in 1 mm increments with a scale reading settings. The mode of operation is to use a thumbscrew setting to position the tips of the caliper pointers at the desired setting. In practice it is possible that errors result in the desired pointer-to-pointer setting due to haste in setting the pointers, wear and tear of the marker components and misreading of the scale reading setting. In addition, surgical tools of these types have non-smooth surfaces and do not preclude hide-out areas that complicate sterilization procedures before reuse. In addition, it is noted that the sharp ends of the prior art caliper tips could result in penetration of the eye scleral limbal conjunctive tissue resulting serious eye injury from bleeding, infections and retinal detachment.

Simplicity is the essential feature of the Melki Marker invention in that it prevents the need for the surgeon to double-check the prior art ophthalmic markers caliper point settings that have been fixed by others. In addition, prior art caliper markers are subject to wear and tear of the setting mechanism that leads to caliper setting gauge inaccuracies after a period of time. By means of using a Melki Marker with a fixed pointer setting the surgeon saves time. The Melki Marker pointer setting is dependent on the type and age of the patient, for example, for an adult, the marker setting points are 3.5 mm apart and for premature infants and infants less than 3 months old, 1.0 mm apart, and for animals, such as racing horses, domestic pets, in the range 2.8 mm to 4.7 mm. These pointer settings are based on the need to ensure that the location of the incision point is in the safe Pars Plana region of the eye.

It is clear to one of ordinary skill in the art that there is a need for an error free, accurate and easy to use marker instrument that ensures the safety of ophthalmic procedures that require marking spots 24 on the scleral surface of the eye without penetration of the conjunctive tissue resulting serious eye injury from bleeding, infections and retinal detachment.

In the preferred embodiment of the invention, the Melki Marker, the pointer set points are fixed for each category of patient whereby errors in pointer setting are eliminated and operating surgeon's time is reduced.

In the preferred embodiment the Melki Marker pointer settings are clearly identified on the instrument distal portion by engraving, imprinting or equal means, as a quality assurance feature to ensure that there is no possibility of using pointer settings in error.

In the preferred embodiment of the Melki Marker the material selected is one from a range of conductive metallic materials that are readily sterilizable and designed with smooth, shiny surfaces.

In a further preferred embodiment of the invention, the Melki Marker is made from materials of reinforced plastics, such as fiber glass, glass reinforced plastic or equal materials, that are less costly to make and can therefore be disposable after use.

In yet a further embodiment of the invention, the Melki Marker is arranged as a disposable once only use instrument having the pre-set pointer positions provided with pre-inked pointer tips with protector thimbles enclosing the ink-tips, and sealed in a sterilized totally see-through and transparent package, ready for immediate use by the operating surgeon pointer settings that are clearly identified on the instrument distal portion by engraving, imprinting or equal identification means.

BRIEF DESCRIPTION OF THE DRAWINGS & TABLE

Figure 1:
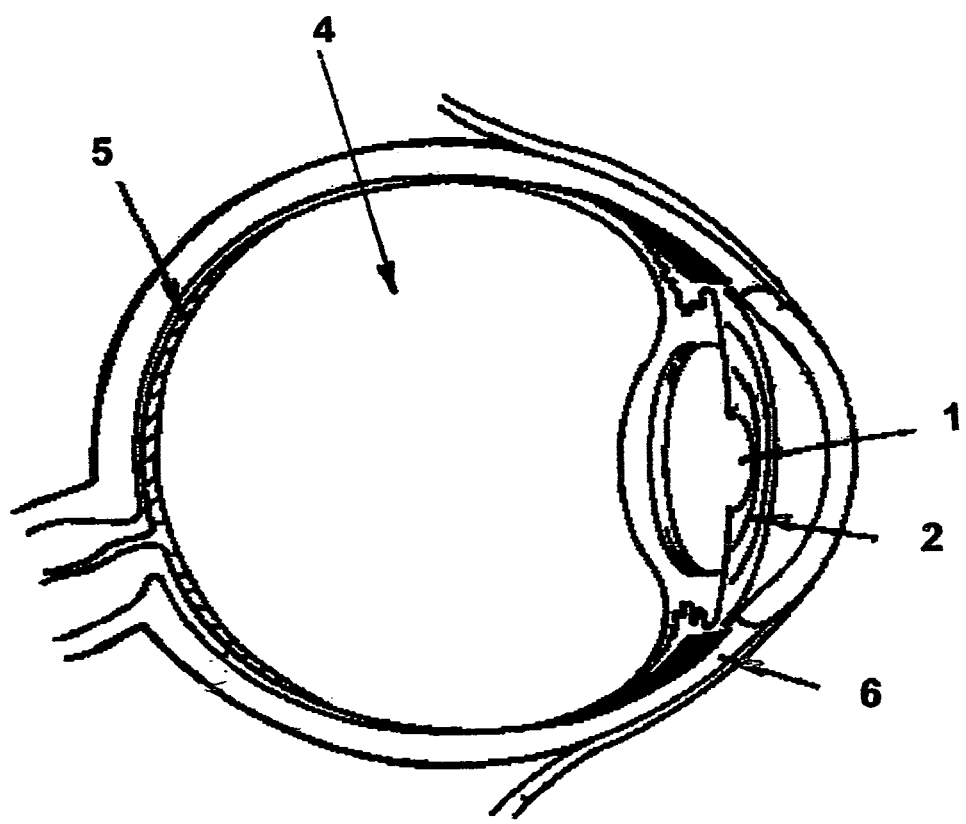

Various features, aspects, and advantages of the present invention will become more apparent with reference to the following Figures and Table accompanying this application, wherein:

FIG. 1—This Figure illustrates the fundamental eye elements for the purposes of performing vitreous retinal surgical procedures for marking incision/injection sites on the sclera limbal tissue.

Figure 2:
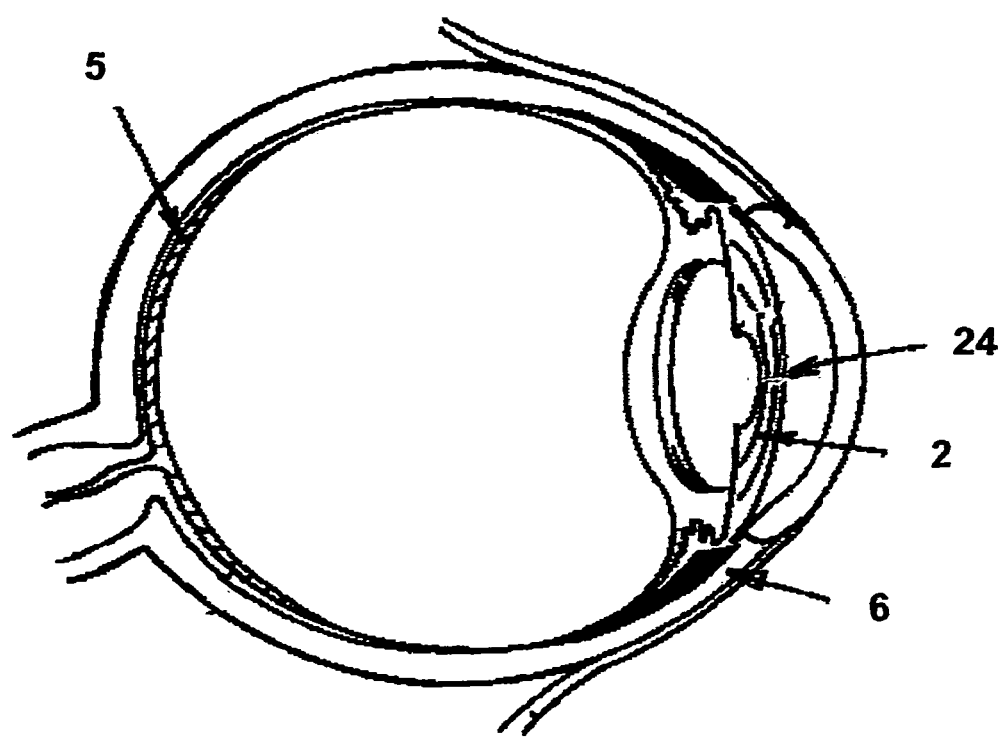

FIG. 2—This Figure illustrates the marking on the scleral surface of the eye at a distance of 3.5 mm from the edge of the iris.

Figure 3:
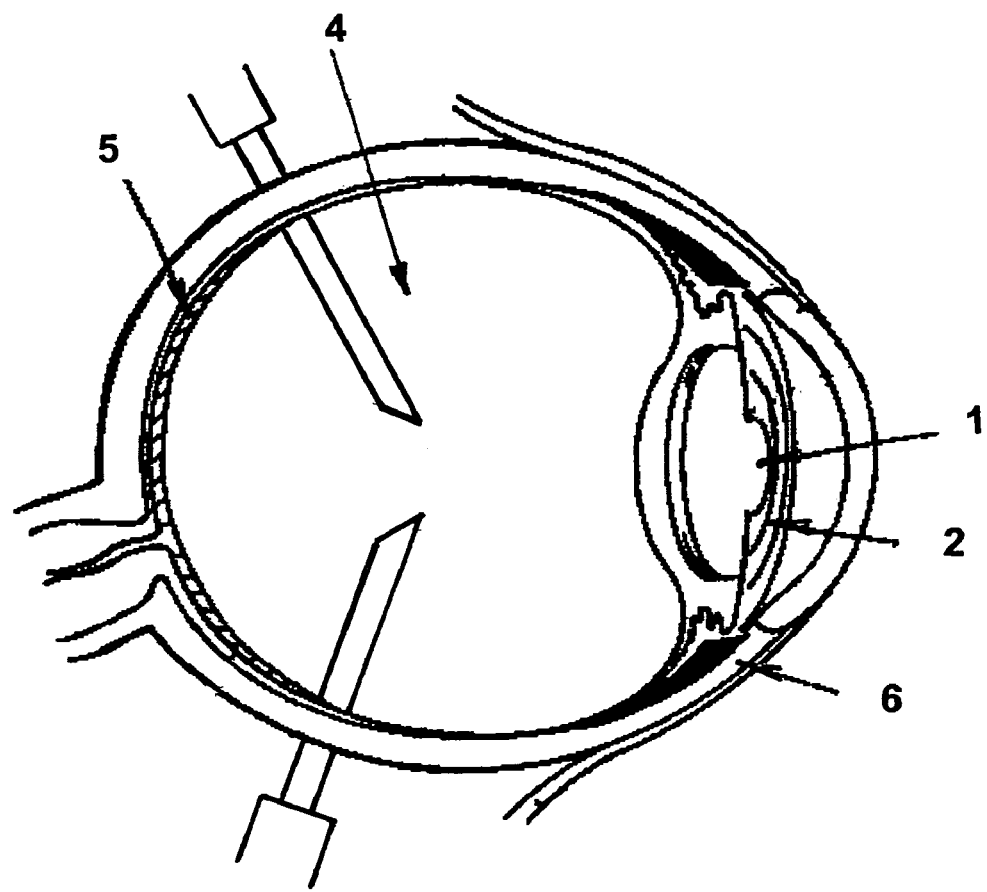

FIG. 3—This Figure shows vitrectomy instrument positions.

FIG. 4—This Figure shows a further example of prior art used in scleral marking procedures.

Figure 5:
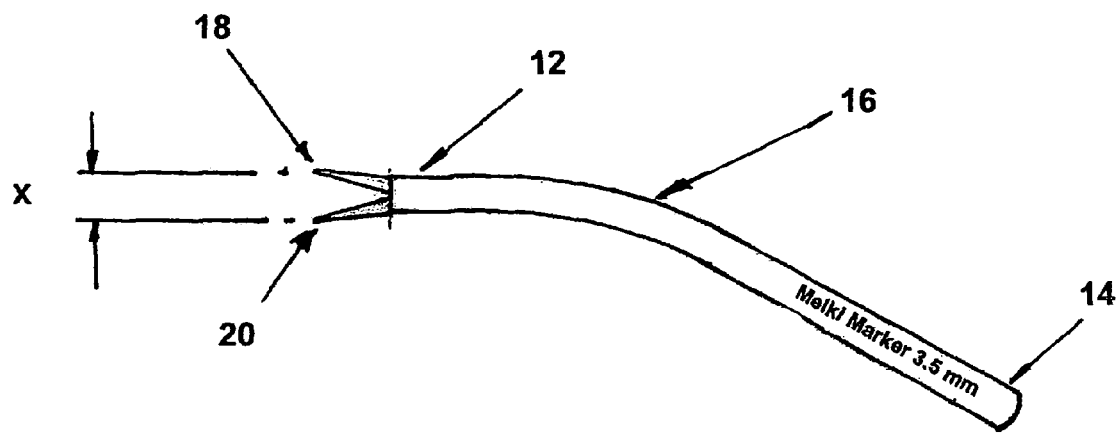

FIG. 5—This Figure shows image of Melki Marker with pointer distances for different patients.

Figure 6:
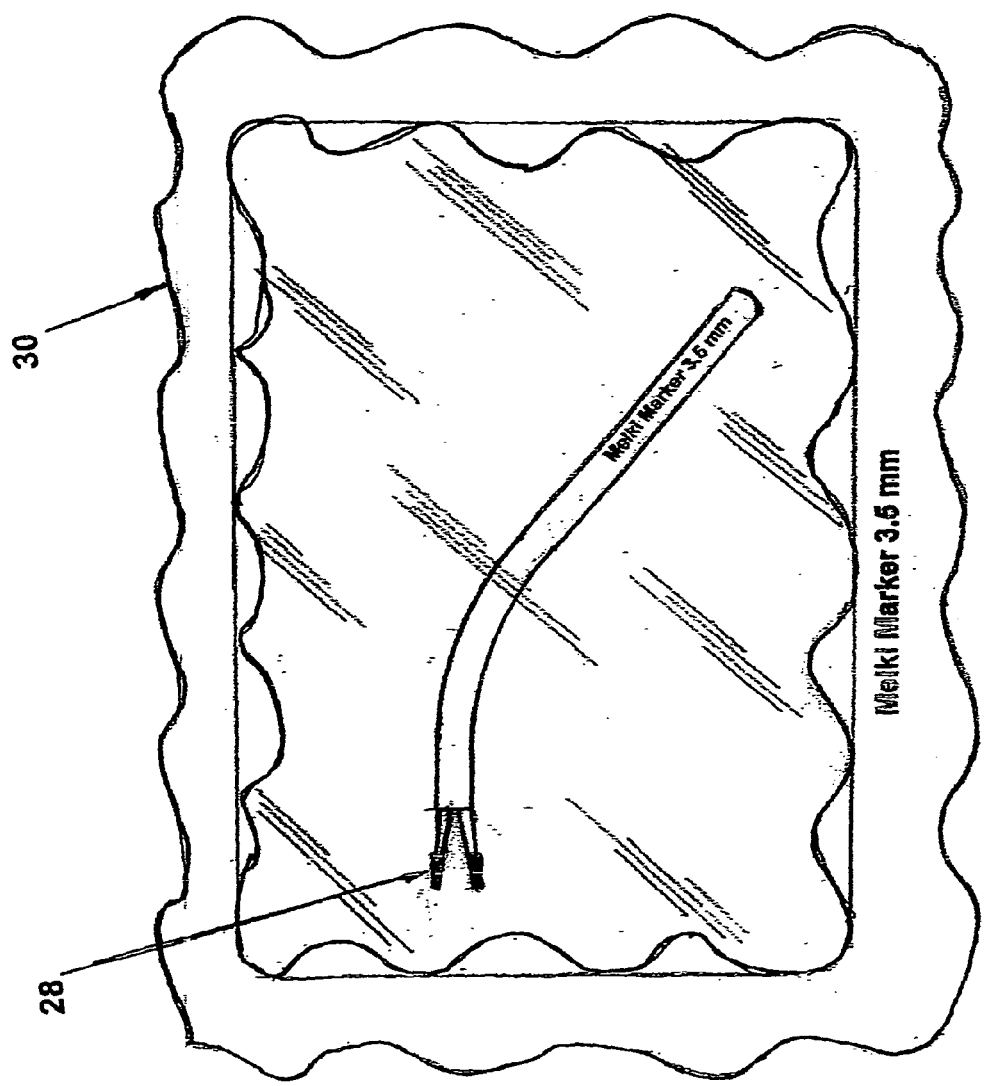

FIG. 6—This Figure shows image of Melki Marker made in plastic or equal material with ink dipped pointers in sealed totally see-through transparent package.

Figure 7:
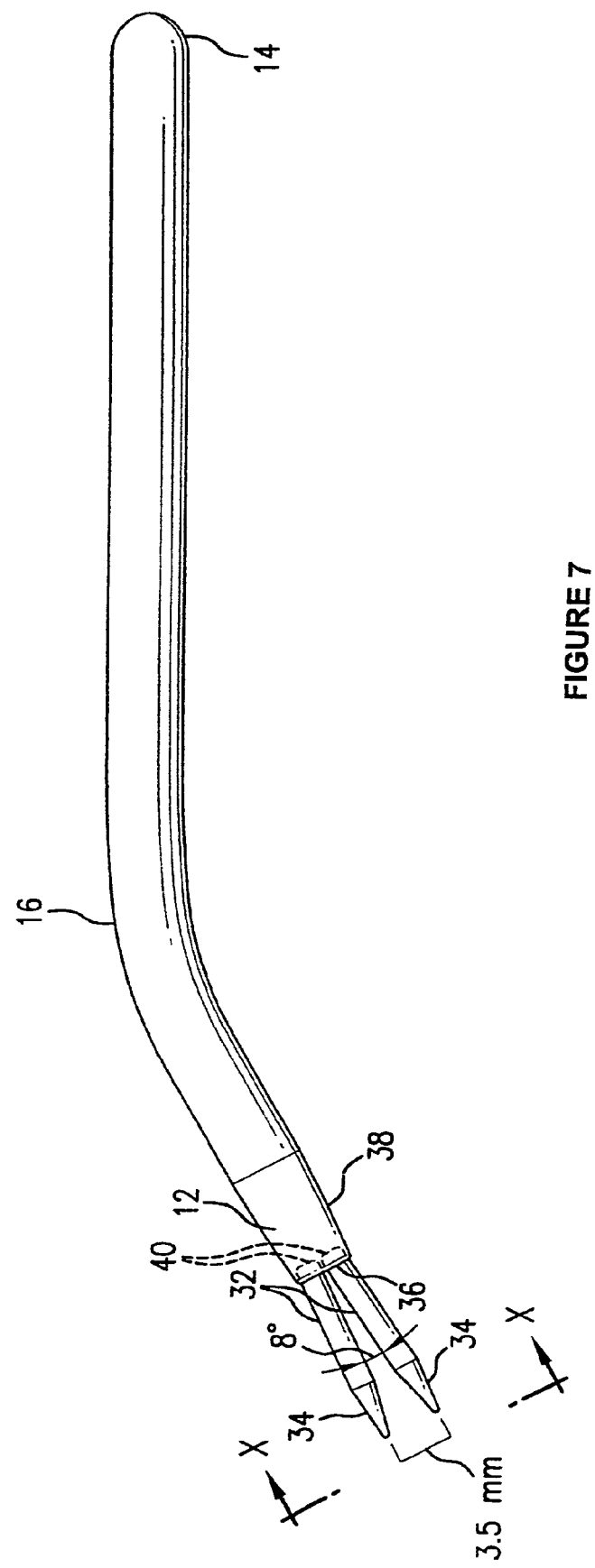

FIG. 7—This Figure shows a detailed drawing of a preferred embodiment of the Melki Marker surgical instrument showing the disposition of the major components.

Figure 8:
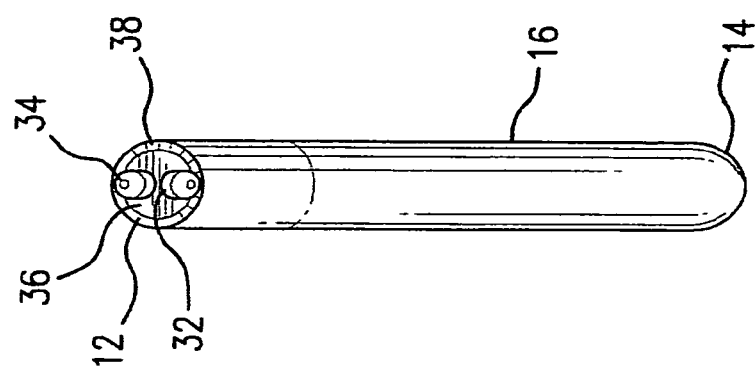
Figure 9:
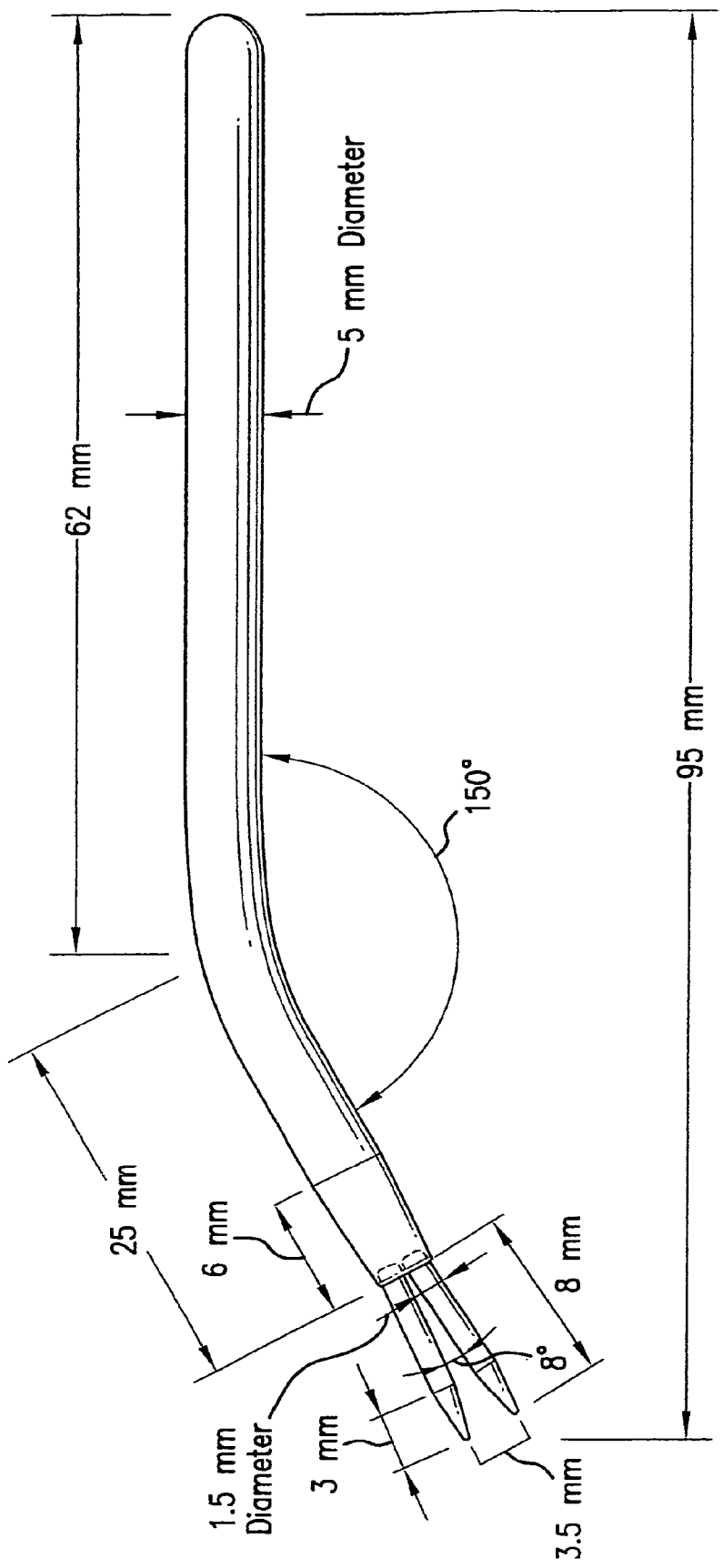

FIG. 8—This Figure shows a preferred embodiment of the Melki Marker surgical instrument with an end view on X-X of FIG. 9.

FIG. 9—This Figure shows a preferred embodiment of a Melki Marker surgical instrument providing typical instrument dimensions in mm. of the major components.

Table 1—Depicts typical steps performed by a surgeon in marking the scleral of the human eye.

LIST OF REFERENCE NUMBERS FOR THE ELEMENTS IN THE DRAWINGS

The following is a list of the elements in the drawings in numerical order.
1 Pupil
2 Iris
4 Vitreous
5 Retina
6 Sclera
10 Surgical Marker
12 Proximal End
14 Distel End
16 Bend Portion
18 Pointer
20 Pointer
22 Eyeball
24 Incision Spot
26 Caliper
28 Protector Thimbles for Pre-Inked dipped Pointers
30 Vacuum Sealed totally see-through transparent Package
32 Distinct cylindrically shaped pointer pins forming pointers 18 and 20 by inserting into the end surface 36 at the proximal end 12
34 Truncated conical shaped blunt ends of pointer pins 32
36 End surface of the proximal end 12 onto which the pointer pins 32 are attached in an angular configuration by insertion into the proximal end 12 by a plurality of means including press fitting, brazing, welding or equal fabrication methods, and in addition in the form of a single piece casting, forging, molding, or equal casting methods
38 End tapered section at the proximal end 12 to facilitate a crimping or equal assembly method to secure the pointer pins 32 within the proximal end 12 section
40 shows the location of the end pointer pins 32 in the secured position within the proximal end 12 section

DETAILED DESCRIPTION OF THE INVENTION

The object of the present invention is therefore to provide a marker for ophthalmic surgical procedures which permits the operating physician to effect a precise marking of the location to be operated upon with accuracy, safety and a reduction in the surgeon's operating time.

For such procedures, the Melki Marker is held by the surgeon in one hand and brought into contact with the sclera limbal tissue of the eye by means of the operating physician taking hold of a tubular marker at the distal handle end, and presenting the two sharp marker pointers or in an alternative embodiment two marker pointers in the form of conical shaped blunt nosed or ended pointer pins, at the proximal end so that two dots/spots 24 may be made on the scleral surface at for example, 3.5 mm apart for adults and in a manner that uses the edge of the iris, also known as limbus, as reference point and ensures that the Pars Plana safety region is maintained. The novel feature of the 'Melki Marker' is that by having a fixed distance between the marker points it is ensured that incision spots 24 made by the pointers are always 3.5 mm apart for adult human procedures. It will be apparent to those skilled in the art that the instant invention can be employed for marking other animal surface tissue for other configurations including global, spherical, solid geometric, three dimensional, and planar shaped organic tissue configurations.

The key embodiment of the Melki Marker is that it is a simple and easy to use surgical instrument that has no moving parts that are intrinsic to prior art caliper markers. The absence of moving parts prevents marker manipulation position settings errors, errors in settings due to wear and tear of the caliper mechanism moving parts, and saves the surgeon the need to double-check the caliper setting for inaccuracies. The embodiment of two marker pointers in the form of conical shaped blunt nosed or ended pointer pins, at the proximal end so that two dots/spots 24 may be made on the scleral surface as detailed in FIGS. 7 to 9 showing specific pointer details 32, 34, preclude penetration of the eye scleral limbal conjunctive tissue that could result in serious eye injury for example, from bleeding, infections and retinal detachment.

There are several ophthalmic procedures that require the surgeon to locate precise incision points on the scleral surface of the eye. For example, for vitrectomies performed in hospital operating rooms, and in out-patient surgical facilities, it is necessary to locate up to three incision spots 24 on the scleral surface wherein each location is required to be in the Pars Plana safety region at exactly 3.5 mm from the edge of the iris as shown in FIG. 2.

The sharp marker pointer ends 12 and 18 or in an alternative embodiment two marker pointers in the form of conical shaped blunt nosed or ended pointer pins 32, 34, are applied with ink by a nurse using sterilized blue ink pen from an epidermic labeler, such as #150 available from Devon Inc., or equivalent non-toxic, waterproof, absorbable ink or stain. In this manner the ink soaked pointers can be placed on the eye ball to mark multiple incision/injection spots 24 on eye scieral surface in settings such as Operating Rooms, where for example, vitrectomy ophthalmic procedures are performed.

There are other ophthalmic surgical procedures that are performed in doctor's offices where the treatment requires the injection of medications such as steroids, anti-biotics, and anti-VEGF and requires similar procedures/injections for the location of injection spots 24.

In a preferred embodiment of the surgical marker the Melki Marker is made from stainless steel or equal conductive metallic material in the form of a solid smooth surface tubular metal rod and arranged with the marker points at exactly 3.5 mm apart for use on adult human eyes as disclosed in FIG. 5. The tubular metal rod can be in the form of a solid, or a hollow structure configured as circular, square, rectangular or other geometric shapes. This embodiment can also be provided with an identification marker (such as "Melki Marker 3.5 mm, or "M-M 3.5 mm") on the handle metallic or plastic surface of the instrument to indicate the pointer setting distance in mm's and this can be applied by engraving, imprinting, stamping, stenciling or other equal identification method.

In a further preferred embodiment the Melki Marker is made from reinforced plastics, such as fiber glass, glass reinforced plastic or equal light weight, high tensile strength materials in the form of a solid smooth surface tubular rod, that is less costly to make than metallic forms and can be disposable after use. This embodiment can also be provided with an identification marker on the handle surface of the instrument to indicate the pointer setting in mm and this can be applied by engraving, imprinting, stamping, and stenciling or other equal identification method.

In yet a further preferred embodiment the distal ends of the sharp pointers 18, 20, markers or in an alternative embodiment two marker pointers in the form of conical shaped blunt nosed or ended pointer pins, 32, 34, are pre-soaked in ink dye from an approved epidermic labeler and protected by rubber, polystyrene or other equal type of material thimbles 20, and packaged for use in a sterilized sealed and totally see-through transparent package 30, as disclosed in FIG. 6. The see-through package 30 is in the form of a totally transparent package whereby the contents are visible on all sides to give a totally see-through capability. In this embodiment the material selection makes it suitable for disposal after use. In addition, in this embodiment the handle metallic or plastic surface portion of the instrument is engraved, stamped, imprinted or other identifying means, with the pointer distances in mm. In addition, the surface of the see-through totally transparent sealed package surface can also be imprinted, stamped, or with equal identification means to indicate to the surgeon the marker pointer distance in mm's.

FIG. 5 shows a specific embodiment of a surgical marker made from high tensile strength material, such as stainless steel, alloy steel, titanium or equal material that can be sterilized. The surgical marker 10 has a tubular distal end 14 with a means for readily handling and a bend portion 16 at an included angle of approximately 150 degrees in a range of about 130 to 160 degrees for an ergonomic configuration, a proximal end 12 with two sharp-ended pointers 18 and 20 or in an alternative embodiment two marker pointers in the form of conical shaped blunt nosed or ended pointer pins, 32, 34, are arranged in a vee formation and set at a fixed distance of 3.5 mm between said pointers 18, 20, 32, 34, in a preferred embodiment for adult patients.

The invention described herein is for a surgical instrument used primarily intended for surgical retinal surgeons. However, the basic concept of the invention could have other applications in other medical specialties with different proximal end pointer 18, 20, settings in excess of 5.00 mm.

The Melki Marker invention incorporates a number of alternative embodiments for the material for making the marker. For example, a preferred embodiment of the surgical marker the material of the marker can be made of alloy steels, stainless steel, nickel-chromium steels, or titanium that can be readily sterilized in the hospital or doctor's office facilities. A further preferred embodiment of the invention incorporates a disposable material, such as fiber-glass, glass reinforced plastic (GRP) or equal light weight high strength materials, for the Melki Marker wherein the marker can be disposed in licensed disposal equipment.

The above developments of the marker tool are indicative of use in medical procedures wherein the marker can be used in both hospital and doctor's office settings. It will be clear from the foregoing specification disclosure and drawings, that the invention of the Melki Marker provides a simple and reliable means for marking incision/injection spots on the scleral limbal tissues of the human and other animal eye surfaces that is easy to use, exactly accurate, not prone to operating room setting errors, and not subject to inaccuracies due to wear and tear of existing caliper marker setting appliances.

The preferred Melki Marker embodiment is made of materials such as stainless steels, alloy steels, titanium or equal high tensile strength conductive metallic materials that provide for instrument re-use after sterilization, is particularly suitable for hospital operating room settings, as disclosed for example, in FIG. 5.

In a further preferred embodiment the Melki Marker made out of low cost, light weight, high tensile strength plastic materials, and disposable after use is suitable for doctor's office settings. This particular embodiment in the form of a pre-packaged instrument as disclosed in FIG. 6 is ideal for use in doctors' offices.

The instant invention of the structure of the Melki Marker surgical instrument is disclosed in detail in FIG. 7. This Figure discloses details of the two distinct cylindrically shaped pointer pins 32 that form the pointers 18 and 20. The pointer pins 32 provide for a solid tubular section inserted and attached to the end surface 36 at the proximal end 12 and terminating in a conical shaped rounded blunt nosed ends 34. It should be noted that the embodiment of the blunt ends 34 preclude penetration of the eye scleral limbal conjunctive tissue when the surgeon applies the step of marking the eye scleral tissue with incision spots 24. Any penetration of the scleral tissue results in serious eye injury for example, from bleeding, infections and retinal detachment.

The mode of insertion and attachment of the distinct cylindrically shaped pointer pins 32 to the end surface 36 of the proximal end 12 can be achieved by a plurality of means including press fitting pins 32 into reception bores in the proximal end surface 36, crimping pins 32 into an opening at the proximal end surface 36, brazing pins 32 into an opening at the proximal end surface 36, welding pointer pins 32 into an opening at the proximal end surface 36, combinations of all the foregoing specified attachment means, or any other comparable metallic fabrication means of securing the said pins 32 to the proximal end surface 36.

The manner in which the pointer pins 32 can be secured within the proximal end 12 is exemplified by a tapered section 38 whereby the said pins 32 can be secured by a crimping or equal metallic fabrication actions to retain the said pins 32 within tapered section 38 to a position depicted by the shadowed outline 40.

The mode of construction of the pointer pins 32, and blunt nosed pointer ends 34 at the proximal 12 can also be achieved by other means than individual positioning of separate 32 pins. These other means include but are not limited to, casting, molding, investment casting, lost wax process or equal means to manufacture a totally monolithic metallic or plastic structure comprising the complete structure of items 10, 12, 14, 16, and pointer pins 32, 34, 36, 38, 40 in a single construction. This mode of one piece monolithic construction can be achieved using conductive metallic materials and also non-metallic materials including high strength plastic materials, and the methods of production include but are not limited to, for example, casting, forging, investment casting, the lost wax casting process, or equal processes.

The instant invention of the Melki Marker is shown generically in FIG. 8 showing an end view on X-X of the FIG. 7 showing in particular the disposition of the separate pointer pins 32 with respect to the proximal end 12.

The instant invention of the Melki Marker in a preferred embodiment is disclosed in FIG. 9 providing typical instrument component measurements with the units measured in metric units. For example, the overall from distal end 14 to the end of blunt nosed pointers 34 is about 95 mm. in a range of 90 mm. to 120 mm., the diameter of the surgical instrument 10 handle is about 5 mm. in a range of 4 mm. to 7.5 mm, the bend 16 is about 150 degrees included angle in a range of 130 degrees to 160 degrees, and the pointer pins 32 are about 1.5 mm. in diameter in a range of 1.00 mm. to 2.5 mm., and the distance between rounded shaped blunt ended pointer pins 34 is 3.5 mm. for treatment of adults. Additionally, the angular configuration of the said pointer pins 32 provides for an included angle of about 8 degrees in a range of 5 to 15 degrees dependent on the linear length of the said pointer pins 32 from the proximal end face 36.

It will be evident to those skilled in the art that the elongated tubular structure 10 can be solid or hollow using conductive metallic and plastic materials and comprising distal end 14, bend 16, and proximal end 12 configuration of the pointer pins 32, rounded shaped blunt nosed ended pointer pins 34, end surface proximal end 36, can be formed in a single monolithic construction using methods including single piece metallic forgings, single piece metallic castings, or equal manufacturing methods.

It will also be evident to those skilled in the art that elongated solid tubular structure 10 using high strength plastic materials and comprising distal end 14, bend 16, the proximal end 12 configuration of the pointer pins 32, rounded shaped blunt nosed ended pointer pins 34, end surface proximal end 36, can be formed in a single monolithic construction using methods including investment plastic casting, plastic molding, or equal manufacturing methods.

While the invention has been described in connection with what is presently considered to be the most practical and preferred embodiments, it is understood that the invention is not limited to the foregoing Detailed Description Drawings of the Invention, and disclosed preferred embodiments, but it will be appreciated by those skilled in the art that the Invention is not limited to the embodiments disclosed, but is capable of numerous rearrangements, modifications, and substitutions of parts or elements without departing from the spirit and scope of the appended Claims.

I claim:

1. A surgical instrument with no moving parts for marking spots at locations on the scleral limbal surface of the eye without penetrating the scleral surface tissue for selecting injection or incision sites, comprising:
   a) an elongated solid tubular structure defining a distal end adapted to being held by a surgeon and a proximal end, the tubular structure having a bend section closer to the proximal end than the distal end of the structure in an ergonomic configuration, and the proximal end incorporating two pointers for marking purposes arranged in an angular vee formation having tips in the form of two equally shaped, diverging, tapered blunt nosed pointers, the pointers connected at an extreme proximal end of the tubular structure, the tips set at a fixed distance apart in the range of 1.00 mm to 5.00 mm, and,
   b) whereby the pointers have a diameter in the range of 1.00 mm to 1.5 mm and whereby the length of the pointers is 8 mm, and,
   c) whereby the pointers are arranged in the vee formation at an angle in the range of 5 to 15 degrees, and,
   d) whereby the elongated structure has no moving parts, and
   e) whereby the instrument is presented by the surgeon to the scleral surface from the said distal end the surgeon is able to accurately scribe an incision spot without penetrating the scleral surface tissue at an exact position based on the fixed distance between the proximal end blunt nosed pointers from the edge of the iris to ensure that the incision is within the Pars Plana without penetrating the scleral surface tissue.

2. The surgical instrument of claim 1 wherein the elongated solid tubular structure is made from stainless steel, alloy steel, titanium or equal high tensile strength conductive metallic material.

3. The surgical instrument of claim 1 wherein the elongated solid tubular structure is made from fiber glass, glass reinforced plastic or other equal light weight and high tensile strength plastic material.

4. The instrument of claim 1 wherein the fixed distance between the tips is 3.5 mm. for adult patients.

5. The instrument of claim 2 or 3 wherein the instrument is packaged in a sterilized vacuum sealed see-through totally transparent package.

6. The instrument of claim 2 wherein the pointers are connected to the end surface of the said proximal end by means of one of crimping, welding, brazing or equal fabrication attachment means.

7. The instrument of claim 2 wherein the whole structure is formed in a single monolithic format from a manufacturing method including one of forging, casting, molding, lost wax process, investment casting process or equal single metallic structure production means.

8. The instrument of claim 3 wherein the whole structure is formed in a single monolithic format from a manufacturing method including one of molding, casting, investment casting or equal single plastic structure production means.

9. A surgical instrument with no moving parts for marking spots at locations on the scleral limbal surface of the eye for selecting injection or incision sites, comprising:
   a) an elongated solid smooth surface tubular structure, and,
   b) the elongated structure defining a distal end adapted to being held by a surgeon and a proximal end, the tubular structure having a bend section closer to a proximal end than the distal end of the structure in an ergonomic configuration, the proximal end incorporating two pointers for marking purposes arranged in a vee formation having tips in the form of two equally shaped, diverging, tapered, blunt nosed pointers connected at an extreme proximal end of the tubular structure, the tips set at a fixed distance of 3.5 mm apart, and,
   c) whereby the pointers have a diameter in the range of 1.00 mm to 2.5 mm and whereby the length of the pointers is 8 mm, and,
   d) whereby the pointers are arranged in the vee formation at an angle in the range of 10 to 15 degrees, and,
   e) whereby the tips are 3 mm long, and,
   f) whereby the said elongated structure has no moving parts, and,
   g) whereby the instrument is presented to the scleral surface by the surgeon to accurately scribe an incision spot at an exact position based on the fixed distance between the pointers from the edge of the iris to ensure that the incision is within the Pars Plana.

10. The surgical instrument of claim 9 wherein the elongated solid tubular structure is made from stainless steel, alloy steel, titanium or equal high tensile strength conductive metallic material.

11. The surgical instrument of claim 9 wherein the elongated solid tubular structure is made from fiber glass, glass reinforced plastic or other equal light weight and high tensile strength plastic material.

12. The instrument of claim 10 wherein the pointers are connected to the extreme proximal end by means of one of crimping, welding, brazing or equal metallic fabrication attachment means.

13. The instrument of claim 10 wherein the whole structure is formed in a single monolithic format from a manufacturing method including one of forging, casting, molding, lost wax process, investment casting process or equal single metallic structure production means.

14. An elongated solid tubular structure without moving parts in an ergonomic configuration comprising:
   a) the elongated structure defining a distal end adapted for hand holding and a proximal end, the structure having a bend section closer to the proximal end than the distal end, and the proximal end incorporating two pointer pins, and,
   b) wherein the pointer pins are in the form of two identical cylindrical rods having tips in the form of tapered conical blunt shapes that are 3 mm. long, and,
   c) the pointer pins have a diameter in the range of 1.00 mm to 2.5 mm and whereby the length of the pointer pins is 8 mm, and,
   d) wherein the pointer pins are configured in a vee formation at an angle in the range of 5 to 15 degrees, and,
   e) wherein the pointer pins are connected to an end surface of the proximal end by means of crimping, and,
   f) wherein the elongated structure has no moving parts.

15. The tubular structure of claim 14 wherein the elongated solid tubular structure is made from stainless steel, alloy steel, titanium or equal high tensile strength conductive metallic material.

16. The tubular structure of claim 14 wherein the elongated solid tubular structure is made from fiber glass, glass reinforced plastic or other equal light weight and high tensile strength plastic material.

17. The tubular structure of claim 14 wherein the vee formation of the pointer pins results in a measured distance between the tips in the range of 1.00 mm to 5.00 mm.

18. The tubular structure of claim 15 wherein the pointer pins are connected to the end surface of the proximal end by means of one of crimping, welding, brazing or equal fabrication attachment means.

19. The tubular structure of claim 15 wherein the whole structure is formed in a single monolithic format from a manufacturing method including one of forging, casting, molding, lost wax process, investment casting process or an equal single metallic structure production means.

20. The tubular structure of claim 16 wherein the whole structure is formed in a single monolithic format from a manufacturing method including one of molding, casting, investment casting or an equal single plastic structure production means.

* * * * *